(12) United States Patent
Robinson et al.

(10) Patent No.: US 8,251,896 B2
(45) Date of Patent: Aug. 28, 2012

(54) ENDOSCOPIC IMAGING DEVICE

(75) Inventors: Joseph P. Robinson, West Lafayette, IN (US); Silas J. Leavesley, Lafayette, IN (US); Peng Xi, Shanghai (CN)

(73) Assignee: Purdue Research Foundation, West Lafayette, IN (US)

( * ) Notice: Subject to any disclaimer, the term of this patent is extended or adjusted under 35 U.S.C. 154(b) by 595 days.

(21) Appl. No.: 12/056,970

(22) Filed: Mar. 27, 2008

(65) Prior Publication Data

US 2009/0012369 A1 Jan. 8, 2009

Related U.S. Application Data (63) Continuation of application No. PCT/US2006/038224, filed on Sep. 29, 2006.

(60) Provisional application No. 60/722,776, filed on Sep. 30, 2005.

(51) Int. Cl.
*A61B 1/06* (2006.01)
*A61B 1/00* (2006.01)
*A61B 1/04* (2006.01)

(52) U.S. Cl. .................. 600/182; 600/123; 600/121

(58) Field of Classification Search .......... 600/109, 600/111, 121, 123, 129, 130, 160, 166, 168, 600/170, 171, 176–178, 182, 476, 478; 362/572, 362/574
See application file for complete search history.

(56) References Cited

U.S. PATENT DOCUMENTS

| | | | | |
|---|---|---|---|---|
| 5,547,455 A * | 8/1996 | McKenna et al. | | 600/113 |
| 5,630,784 A * | 5/1997 | Siegmund et al. | | 600/160 |
| 5,919,128 A * | 7/1999 | Fitch | | 600/166 |
| RE36,434 E * | 12/1999 | Hamlin et al. | | 600/109 |
| 6,322,498 B1 * | 11/2001 | Gravenstein et al. | | 600/120 |
| 6,465,968 B1 * | 10/2002 | Sendai | | 315/169.3 |
| 7,011,625 B1 * | 3/2006 | Shar | | 600/109 |
| 7,310,095 B2 * | 12/2007 | Matsumoto | | 345/419 |
| 2003/0045780 A1 * | 3/2003 | Utsui | | 600/182 |
| 2003/0191368 A1 * | 10/2003 | Wang et al. | | 600/160 |
| 2008/0294002 A1 * | 11/2008 | Xie | | 600/109 |

FOREIGN PATENT DOCUMENTS

JP 01310637 A * 12/1989

* cited by examiner

*Primary Examiner* — Philip R Smith
*Assistant Examiner* — William Chou
(74) *Attorney, Agent, or Firm* — Brinks Hofer Gilson & Lione (57) ABSTRACT

An endoscopic imaging device for endoscopy in a body vessel is disclosed. The device comprises an annular illumination tube comprising an annular illumination fiber for illuminating a body vessel during endoscopy. The device further includes a first imaging tube comprising a first imaging fiber for gross examination and navigation through the body vessel. The first imaging fiber is disposed within the annular illumination tube. The device further comprises a second imaging tube comprising a second imaging fiber for cellular imaging. The second illumination fiber is disposed adjacent the first imaging tube and within the annular illumination tube.

18 Claims, 5 Drawing Sheets

ENDOSCOPIC IMAGING DEVICE

CROSS-REFERENCE TO RELATED APPLICATIONS

This application is a continuation of International Application No. PCT/US2006/038224 filed on Sep. 29, 2006, entitled "ENDOSCOPIC IMAGING DEVICE" and claims the benefit of U.S. Provisional Application Ser. No. 60/722,776 filed on Sep. 30, 2005, entitled "ENDOSCOPIC IMAGING DEVICE," the entire contents of each are incorporated herein by reference.

BACKGROUND OF THE INVENTION

This invention relates to the field of endoscopy and more particularly to endoscopic devices that utilize fiber optic detection of fluorescence.

Endoscopes are employed as a routine clinical macroscopic examination tool. One of the most common methods for producing high-quality, optically sectioned, microscopic images, confocal microscopy employs a pinhole or multiple pinholes to capture image data from a specific optical section. Moreover, a confocal raster scanning endoscope scans the tip of a fiber bundle to reconstruct a high-resolution image. With this method, an image is taken in the forward-facing direction of the endoscope. Although adequate, this configuration limits the endoscope to operation in situations where a surface plane orthogonal to the tip of the endoscope is encountered. Furthermore, in this configuration, the imaging lens used for confocal and widefield imaging is typically the same lens, limiting the spatial confocal resolution.

Thus, there is a need to improve endoscopic devices being used to obtain images in the forward-facing direction and the lateral direction relative to a passage within a vessel.

BRIEF SUMMARY OF THE INVENTION

The invention describes an imaging endoscope that enhances features of an endoscope and combines both macroscopic and confocal microscopic capabilities. A unique aspect of the present invention is the use of a fiducial coordinate system to relate the macroscopic and microscopic images.

An improved endoscope, offering the ability to image tissues in vivo on both a gross and a cellular level is provided. Embodiments of the present invention allow the user to effectively select an area of interest in a macroscopic view and "zoom-in" to view cellular information from the same area. For medical doctors or veterinarians, this will make possible an immediate histological identification without the need to surgically extract biopsy samples. In many cases, the present invention may effectively reduce the need for biopsy, reducing examination time, expense, and discomfort for the patient. Features of the present invention also allow physicians to examine suspected tissues in a much more methodical and thorough method than is allowed through traditional biopsy. Another component of this product is the methods of software that enables the operation of this device.

In one embodiment, the present invention provides an endoscopic imaging device for endoscopy in a body vessel. The device comprises an annular illumination tube including an annular illumination fiber for illuminating a body vessel during endoscopy. The device further comprises a first imaging tube comprising a first imaging fiber for gross examination and navigation through the body vessel. The first imaging fiber is disposed within the annular illumination tube. The device further comprises a second imaging tube comprising a second imaging fiber for cellular imaging. The second illumination fiber is disposed adjacent the first imaging tube and within the annular illumination tube.

In another embodiment, the present invention provides an endoscopic assembly for endoscopy in a vessel. The assembly comprises the device and a control system for defining cylindrical image data from video data of gross video images and image data of cellular images of the vessel from the insertion tube and for converting the cylinder image data to a 2-dimensional map for imaging tissues on both a gross level and a cellular level.

In another example, the present invention provides a method of endoscopic imaging for endoscopy in a vessel. The method comprises introducing the endoscopic imaging device for endoscopy and illuminating the vessel for endoscopy. The method further comprises receiving video data of gross video images and image data of cellular images of the vessel from the insertion tube and converting the data to a 3-dimensional imaging data in cylindrical coordinates, defining a cylindrical image data. The method further comprises converting the cylinder image data to a 2-dimensional map for imaging tissues on both a gross level and a cellular level.

Further objects, features, and advantages of the present invention will become apparent from consideration of the following description and the appended claims when taken in connection with the accompanying drawings.

BRIEF DESCRIPTION OF THE DRAWINGS

FIG. 2b is a cross-sectional view of the insertion tube taken along line b-b in FIG. 2a;

DETAILED DESCRIPTION OF THE INVENTION

Embodiments of the present invention incorporate multiple single-mode imaging fibers, allowing for simultaneous imaging at both a gross level and a cellular level. One example of the present invention provides a trifurcated fiber design with two imaging fibers and one illumination fiber branching apart near the proximal end of the device. Distal to the trifurcation point, the annular illumination fiber encloses both of the imaging fibers. Each fiber is fitted with a specific adapter to allow coupling of the fiber to the desired video and imaging cameras or light source.

Figure 1:
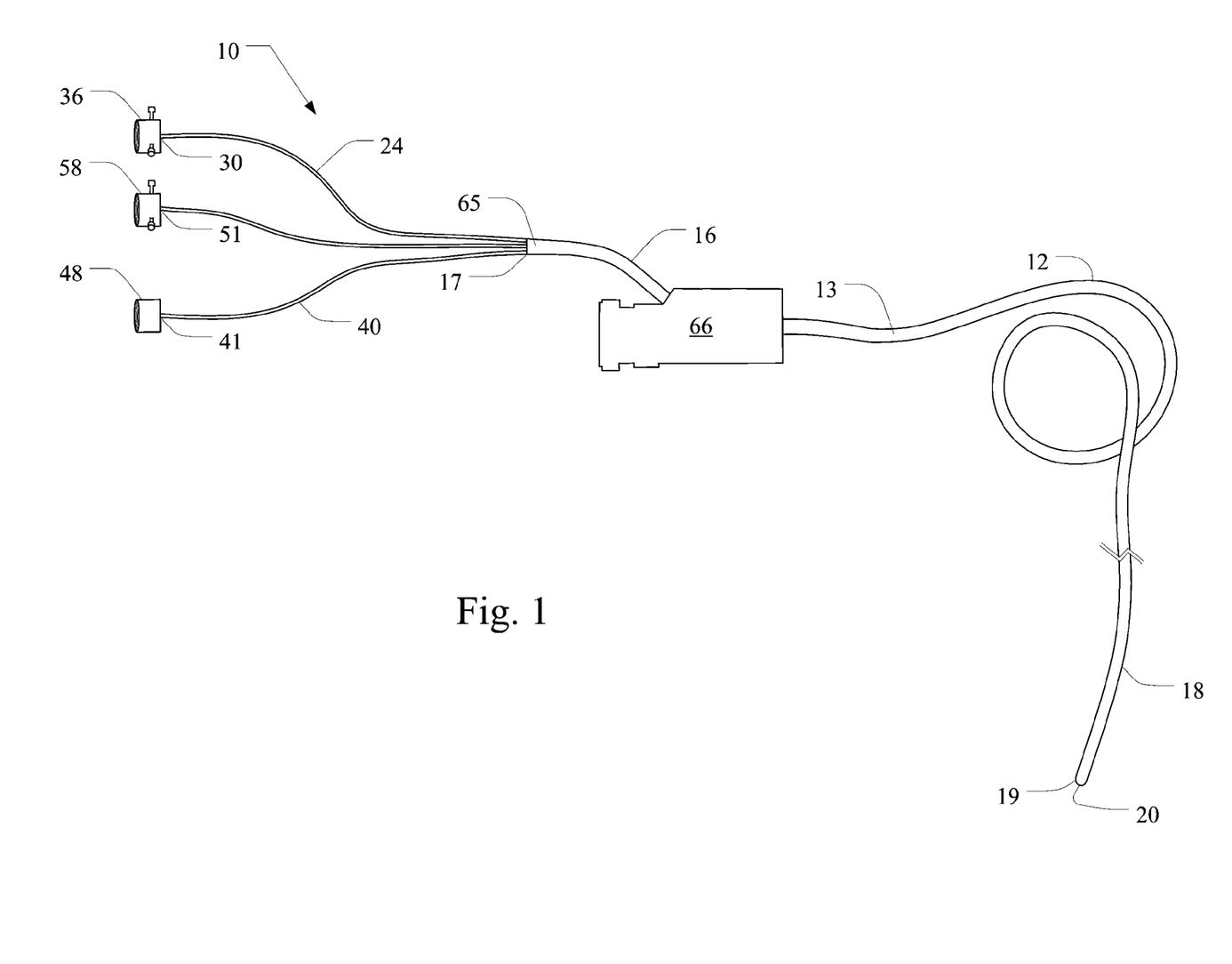
FIG. 1 is a schematic view of an endoscopic imaging device in accordance with one embodiment of the present invention.

FIG. 1 illustrates an endoscopic imaging device 10 for endoscopy in a vessel, e.g., a body vessel of a patient. As shown, the device comprises an insertion tube 12 including and outer layer 13, preferably made of polytetraethylene, and an outer sheath 14 having a proximal portion 16 with a proximal end 17 and a distal portion 18 with a distal end 19. The distal end 19 has an open distal tip 20 that is preferably beveled or tapered and is open to allow for gross examination and navigation with video imaging therethrough. In this example, the open distal tip 20 includes an opening 22 formed therethrough and having a distal window 23 disposed at the opening 22 to allow for imaging, e.g., gross video imaging, therethrough of the vessel.

Figure 2A:
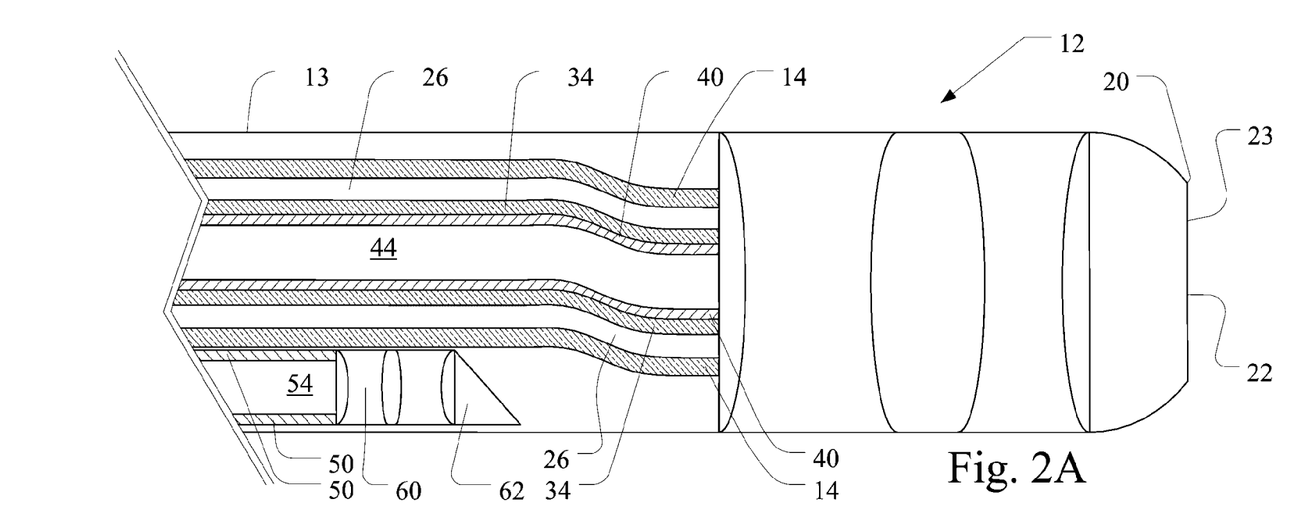
FIG. 2a is a partial side view of an insertion tube of the endoscopic device of FIG. 1.
Figure 2B:
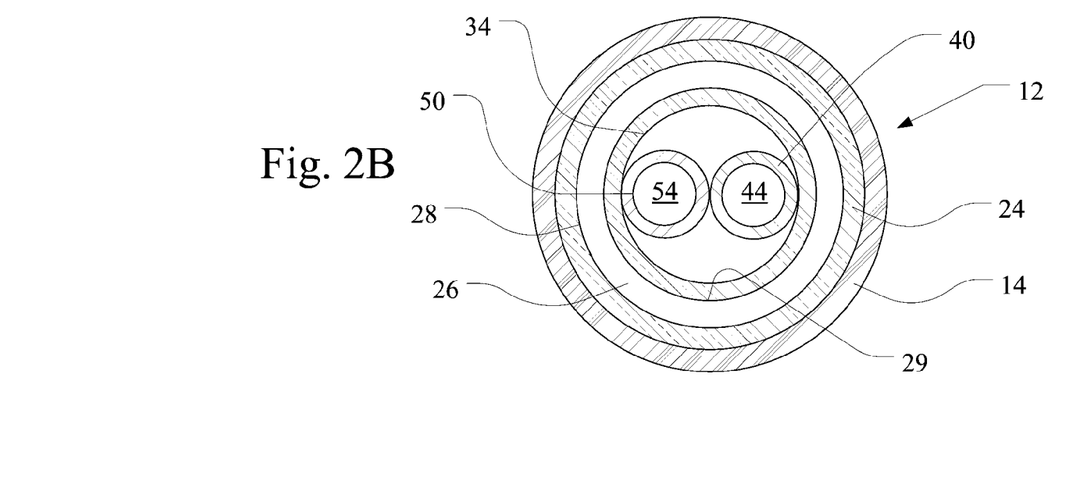

FIGS. 1-2b illustrate that the endoscopic imaging device further comprises an annular illumination tube 24 which preferably is an outer illumination cladding disposed on the inside surface of the outer sheath and extends therethrough. The annular illumination tube 24 further has an annular illumination fiber 26 disposed within the outer illumination cladding. In this embodiment, the annular illumination fiber 26 comprises a plurality, e.g., thousands, of illumination fibers bundled together to form an annular shape. The annular illumination fiber includes an outer surface 28 and an inner surface 29. In this embodiment, the annular illumination fiber 26 comprises a first or proximal end and a second or distal end. The annular illumination fiber 26 is preferably coaxially disposed through the illumination cladding so that the outer surface 28 of the annular illumination fiber 26 is in contact with the illumination cladding. The annular illumination fiber 26 further has an inner illumination cladding 34 disposed on the inner surface 29 of the annular illumination fiber 26 to allow a light source (discussed below) to transmit illuminating light therethrough. In use, the annular illumination fiber 26 illuminates the vessel during endoscopy.

At its proximal end, the annular illumination fiber 26 has an illumination adaptor 36 connected thereto and to an illumination source for illumination of the vessel. In this embodiment, the illumination source is in optical communication with the annular illumination fiber 26 by way of the illumination adaptor 36. In one example, the annular illumination tube 24 is coaxially disposed through the outer sheath 14 so that the distal tip 20 of the outer sheath 14 is in longitudinal alignment with the second end of the annular illumination fiber 26. Being open, the distal tip 20 allows for light to be transmitted therethrough for illumination of a passage in the vessel.

In one embodiment, the annular illumination tube has a diameter of between about 1 and 5 millimeters. However, the diameter of the annular illumination tube may differ (e.g., up to or greater than 1 inch) based on the diameter size of the vessel through which it is disposed, without falling beyond the scope or spirit of the present invention. Also, in this embodiment, the distal portion of the annular illumination tube is between about 10 and 100 centimeters. Of course, other sizes (e.g., up to or greater than 3 meters) may be used based on the length of the vessel in which the device is disposed, without falling beyond the scope or spirit of the present invention.

The device 10 further comprises a first imaging tube 40 having a proximal end 41 and a distal end. In this embodiment, the proximal and distal ends are open. The first imaging tube 40 further includes a first imaging fiber 44 for gross examination and navigation through the vessel. The first imaging fiber 44 includes proximal and distal parts. Preferably, the first imaging fiber 44 is coaxially disposed through the proximal end 41 of the first imaging tube 40 and runs to its distal end. As shown, the first imaging tube 40 is in partial contact with and disposed within the inner illumination cladding 34. In this embodiment, the first imaging tube 40 is in an off-centered or a non-coaxial relationship with the annular illumination fiber 26 and runs thereacross. The first imaging tube 40 terminates at its distal end preferably in substantial alignment with the distal end of the annular illumination fiber 26 and the distal tip 20 of the outer sheath 14.

At its proximal part, the first imaging fiber 44 has a first adaptor 48 connected thereto and to a video imaging source for gross video imaging of the vessel. In this embodiment, the video imaging source is in optical communication with the first imaging fiber 44 by way of the first adaptor 48 for gross examination and navigation through a passage within the vessel. In use, a gross widefield image is preferably a video-rate feed. This image may be used for gross examination and navigation through the vessel and is acquired by means of the forward-facing, distal window. As shown in FIGS. 2a and 2b, the illumination is provided via the annular illumination fiber.

As shown in FIGS. 1-2b, the device 10 further comprises a second imaging tube 50 having a first or proximal portion 51 and a second or distal portion. The second imaging tube 50 further includes a second imaging fiber 54 for cellular imaging within the vessel. The second imaging fiber 54 includes proximal and distal sections. Preferably, the second imaging fiber 54 is coaxially disposed through the proximal portion 51 of the second imaging tube 50 and runs to its distal portion. As shown, the second imaging tube 50 is in partial contact and disposed within the inner surface 29 of the annular illumination fiber 26. Moreover, the second imaging tube 50 is disposed adjacent the first imaging tube 40. In this embodiment, the second imaging tube 50 is in an off-centered or non-coaxial relationship with the annular illumination fiber 26. At its proximal section, the second imaging fiber 54 has a second adaptor 58 connected thereto and to a cellular imaging source for cellular imaging of the vessel. In this embodiment, the cellular imaging source is in optical communication with second imaging fiber by way of the second adaptor.

Figure 4:
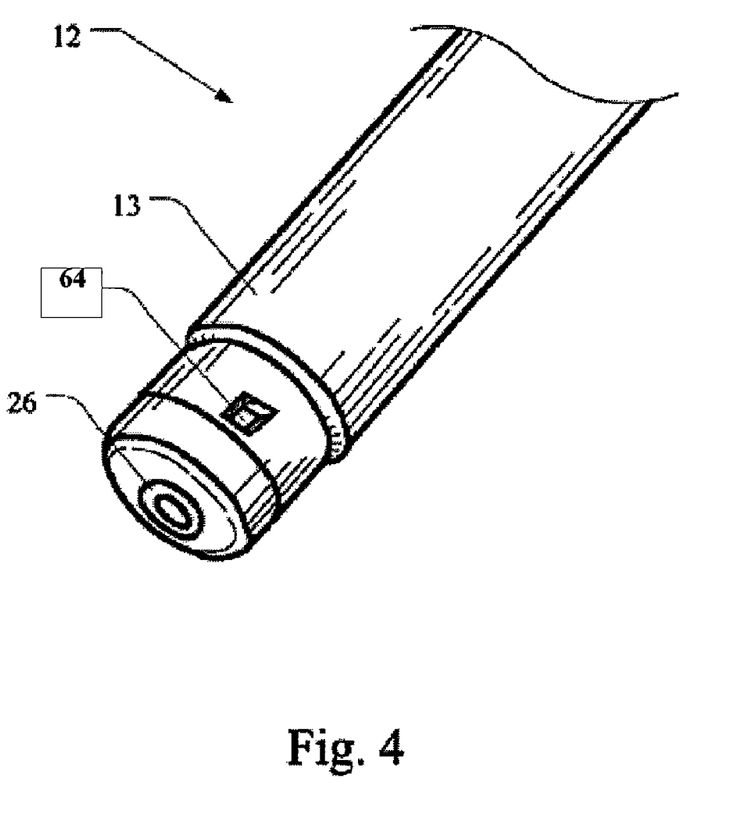
FIG. 4 is a perspective view of the endoscopic device in FIG. 2b.

FIGS. 2a-b and 4 depict the second imaging fiber 54 and tube 50 extending through the sheath 14 and terminates at the distal portion 18 of the sheath 14 proximal to the distal tip 20 thereof. Preferably, the second imaging fiber 54 extends through the illumination tubes by way of bores formed therethrough. The second imaging fiber 54 further extends through the annular illumination fiber 26 since the fiber 26 is comprised of a bundle of fiber optic members in this example as mentioned above. As shown, the outer sheath 14 further includes a cellular imaging microlens 60 and a right angle prism 62 disposed therein. In this example, the microlens 60 is disposed at the distal portion 18 of the sheath 14 and positioned distal to the second imaging fiber 54 and in axial alignment therewith. The right angle prism 62 is positioned distal to the microlens 60 in axial alignment therewith. As shown, the sheath 14 comprises a side imaging port window 64 also formed at the distal portion 18 of the sheath 14 and positioned in radial alignment with the right angle prism 62 for radial or lateral cellular imaging of the vessel during endoscopy.

At the proximal end 17 of the outer sheath 14, the annular illumination tube 24 proximally extends therefrom, and the first and second tubes separate from the annular illumination tube, defining a trifurcation portion 65. It is to be understood that the first and second tubes may be configured to separate from the annular illumination tube at the trifurcation portion by any suitable means without falling beyond the scope or spirit of the present invention. For example, the illumination tube may include bores through which the first and second tubes extend to separate therefrom. The first and second tubes that extend through the annular illumination fiber 26 being a bundle of fiber optic members.

It is to be noted that the annular illumination tube, the first imaging tube, and the second imaging tube are each preferably comprised of polyethylene, polypropylene, or polytetrafluoroethylene, or a mixture thereof. However, any other suitable material may be used without falling beyond the scope or spirit of the present invention.

Figure 3:
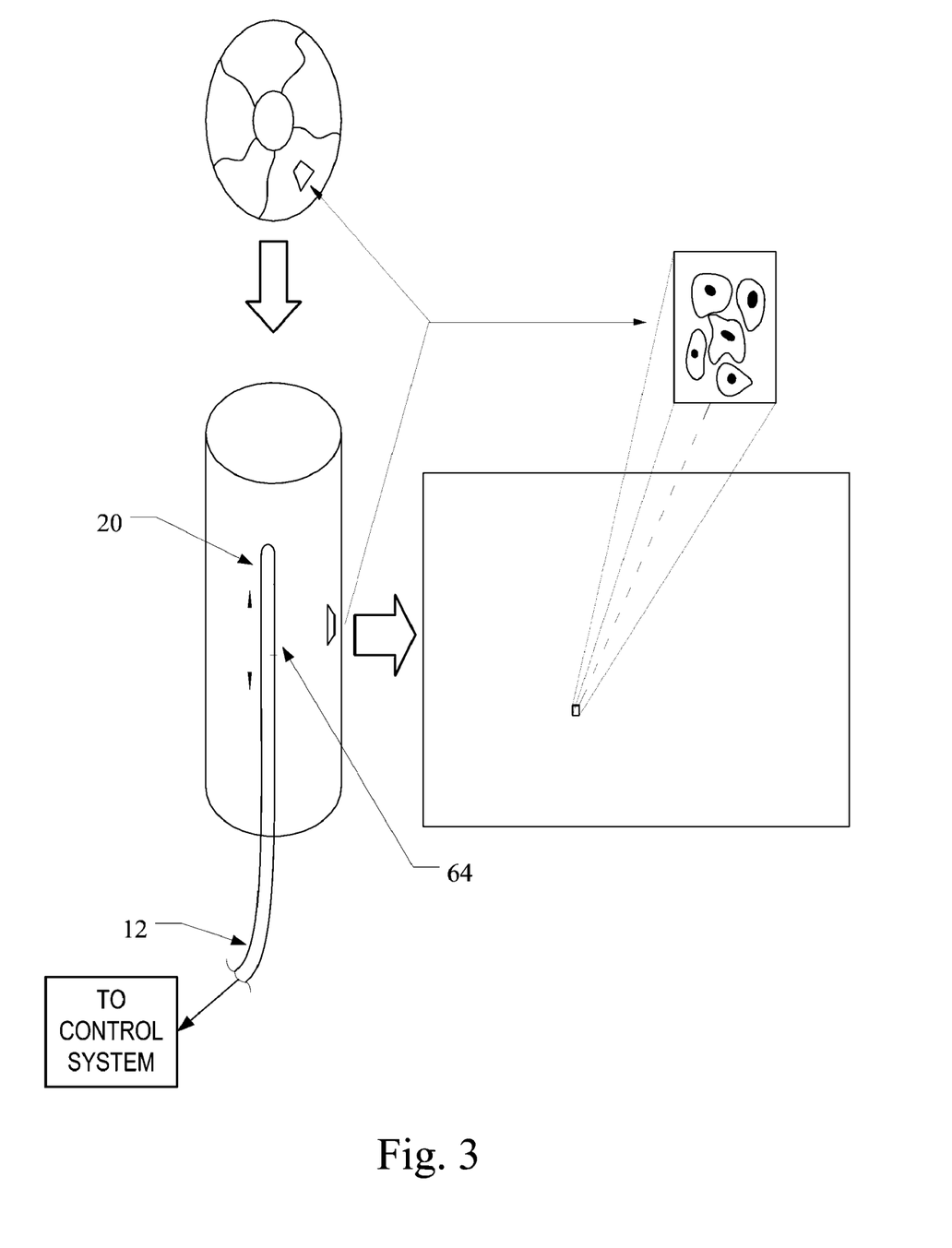
FIG. 3 is a schematic view of software and image correlation of the endoscopic device in accordance with one example of the present invention.

The cellular image, which may or may not be video rate, may be used to obtain images of a section of tissue with a field of view of preferably, but not necessarily, between about 0.3 and 1 mm, and more preferably about 0.6 mm. The images obtained may also have a resolution of preferably between about 2 and 5 µm, and more preferably about 3.5 µm. As shown in FIGS. 2a and 3, proximal to the distal tip 20 of the outer sheath 14, the cellular imaging fiber terminates from inside the sheath 14 and is coupled to the microlens 60, which is aligned with the prism 62, and in turn, in optical communication with the imaging window 64. Thus, the cellular images are obtained laterally or radially at the side of the insertion tube 12 rather than in the forward-facing direction. This configuration is well-suited for imaging the walls of a tube or a body vessel, such as through the digestive or bronchopulmonary systems. The resolution, dependent on the type of imaging fiber used, is sufficient for histological classification.

In this embodiment, the device 10 further comprises a rotatable handle 66 connected to the insertion tube 12. Disposed about the insertion tube 12 at the trifurcation point 65, the rotatable handle 66 is configured to allow rotation of the insertion tube 12 of at least 180 degrees within the vessel, e.g., a body vessel of a patient, during operation of the device 10. The 180 degree rotation feature ensures that the side imaging window 64 for cellular imaging can be rotated to image essentially any part of the passage through which the endoscopic device 10 moves. The handle 66 is attached to the insertion tube 12 by any suitable means without falling beyond the scope or spirit of the present invention. For example, the rotatable handle 66 may simply be configured to dispose about and receive the insertion tube, and provide the clinician with an ergonomically usable apparatus to allow the clinician to more easily grip and manipulate the insertion tube 12 rather than merely gripping the insertion tube 12 alone.

Preferably, the device is associated with a control system that is in communication with the insertion tube and the components therein mentioned above for receiving data of the vessel and for imaging the data during operation of the device. In one embodiment, the control system includes a computer system with a graphic interface that implements image processing software. The software generally serves as a tool to manage aspects of a multimodal endoscope system. For example, the control system is configured to manage an imaging system for collection of forward and side-port images, but it also manages a navigation system for spatial integrity of the images. The control system is also configured to register both types of images within the context of a pseudo-3-dimensional space. This space is defined by known movements of the endoscope that are measured by an optical navigation system. These measurements may be defined with respect to a relative position (i.e. entrance point of the endoscope), but could also be combined with other types of medical imaging (CT, MRI, ultrasound, X-ray) to yield measurements within an absolute fiducial system.

In one embodiment, the control system includes an optical tracking system. The optical tracking system may be comprised of equipment typically found in conventional high-grade optical mice (i.e. a gaming mouse). This may include a small infra-red diode laser, a detector (high-speed CMOS chip), and some simple firmwear. A relay lens system and supplementary optics may pass an infrared laser into the endoscopic device. Reflected signal may be imaged by the CMOS chip. In this embodiment, software imbedded into the optical mouse (firmwear) performs object tracking analysis similar to that used in some forms of particle image velocimetry (PIV). Parameters within this software may be adjusted to accommodate the endoscope optics and magnification. The signal out may be comprised of Cartesian displacement vectors. Such vectors may be converted to cylindrical space. This type of system is capable of hundreds to thousands of measurements per second, and thus a known position may be recorded for each macroscopic and each microscopic image collected. It is to be noted that there are multiple variations on this system without falling beyond the scope of the present invention, including detection markers on the endoscope with optical, electronic or other sensors at fixed interval spaces that may be interrogated by an internal or external sensor that will facilitate navigation.

Macroscopic and microscopic images are then collected using a driver-interface with the cameras/detectors. In this example, each image will have an associated relative spatial position. This may be accomplished as mentioned above. The field-of-view, resolution, and pixel size of each image will also be known through optical calibration of the system. The macroscopic images will be processed to produce a reconstruction of the wall of the vessel or organ through which the endoscope is traveling. This reconstruction will be visible as either a 3-dimensional volumetric reconstruction or a 2-dimensional "map" of the surface of the organ. The microscopic image data will then be overlayed onto the 2-dimensional organ map (FIG. 3).

In addition to image registration, the 2-dimensional organ map may be used to identify and tag areas for further microscopic imaging. The user will be given the option to mark a specific location in the 2-dimensional organ map. This mark will be converted to a spatial position in cylindrical coordinates (a distance plus an angle of rotation). When the endoscope reaches the desired position, a notice will be issued (auditory, visual, or both), signaling the user to image this area with the microscopic imaging port. A variety of modifications of this concept will allow for the development of an intelligent navigation system that will enhance clinical imaging.

As shown in FIG. 3, through the image processing software, video data of gross video images (via the first imaging fiber) and image data of cellular images (via the second imaging fiber) from the endoscopic device in the vessel is first converted to 3-dimensional imaging data in cylindrical coordinates, defining a cylinder image data. The cylinder image data is of a tube having inner walls. The cylinder image data, describing the passage through which the endoscopic device moves, may then be converted to a 2-dimensional map of the inner walls of the tube.

Since the distance between points on the field of view of the cellular imaging fiber and the gross imaging fiber are known, the control system correlates predetermined points of the cellular and gross images. This enables an examiner to overlay a cellular image on a gross image at any point along the path of travel of the device. Through the use of the cylindrical fiducial coordinate system, the control system also allows an examiner to note the coordinates of areas for further inspection using the gross video images and then to return and perform the cellular imaging once the gross imaging has been completed. This system may be used for examining any surface in a vessel or a tube, e.g., for material fatigue.

Embodiments of the present invention provide an improved endoscope that offers the ability to image tissues in vivo on both a gross and a cellular level. The endoscopic device of the present invention allows the user to perform and complete a macroscopic examination of a vessel, and selectively return to an area of interest in the macroscopic view and "zoom-in" to view cellular information within the same area. For medical doctors or veterinarians, this feature provides the possibility for an immediate histological identification without the need to surgically extract biopsy samples. In many cases, the device may effectively reduce the need for biopsy, reducing examination time, expense, and discomfort for the patient. The device also allows physicians to examine suspected tissues in a much more methodical and thorough method than is allowed through traditional biopsy.

Figure 5:
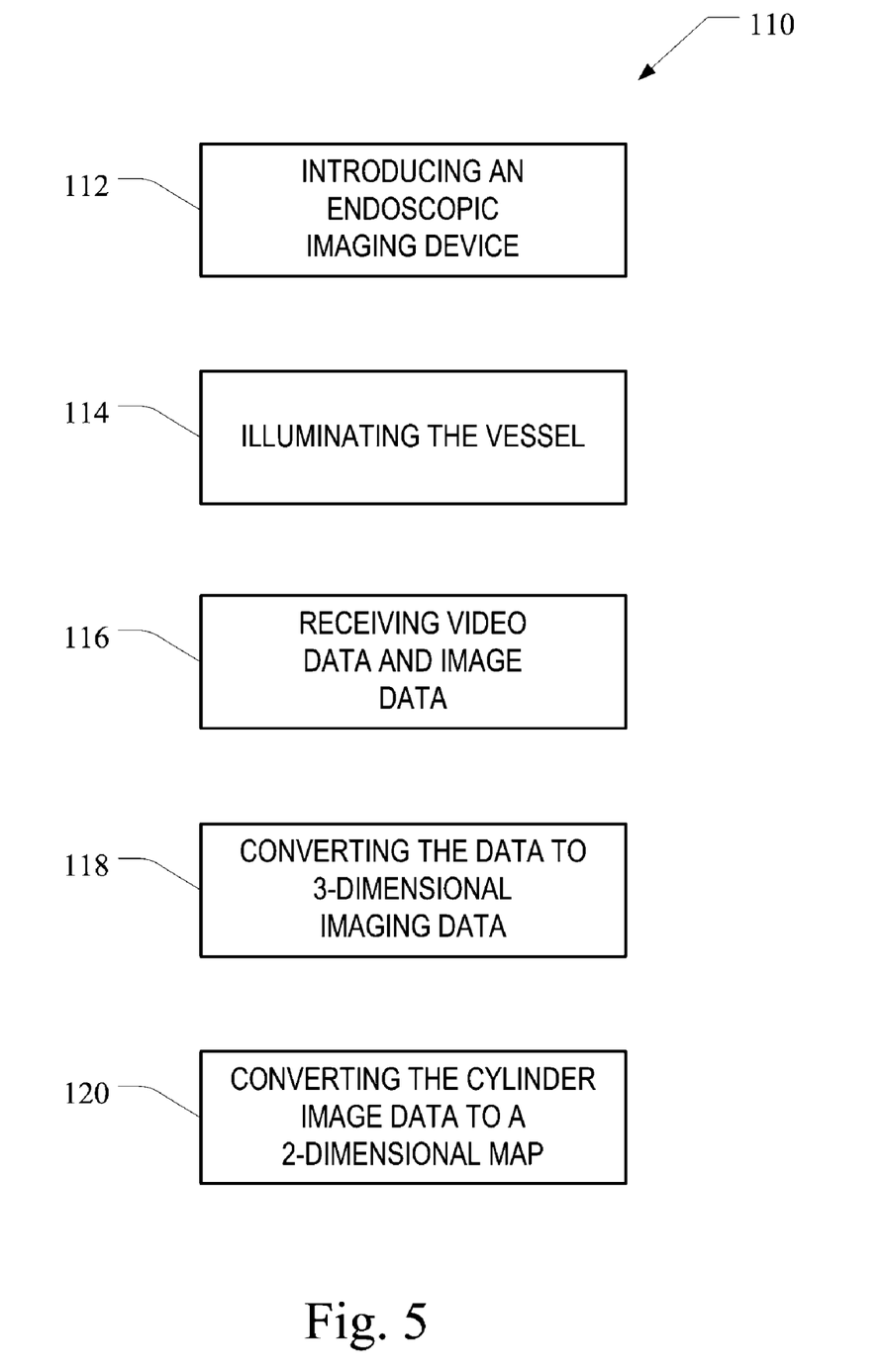
FIG. 5 is a method of endoscopic imaging for endoscopy in a vessel in accordance with one example of the present invention.

FIG. 5 depicts one method 110 of endoscopic imaging by implementing the device mentioned above in accordance with one example of the present invention. As shown, the method 110 comprises introducing the insertion tube of the imaging device to a location for examination in a vessel in box 112 and illuminating the vessel for endoscopy in box 114. The method 110 further includes receiving video data of gross video images and image data of cellular images of the vessel from the insertion tube in box 116. The method 110 further comprises converting the data to a 3-dimensional imaging data in cylindrical coordinates in box 118, defining a cylinder image data. This is accomplished with the distance between the video data and image data. The control system correlates the distance represented by the data of the cellular and gross images. This may be accomplished as discussed above. The method further comprises converting the cylindrical image data to a 2-dimensional map in box 120. This may be accomplished as also discussed above. Other ways may be implemented with falling beyond the scope or spirit of the present invention.

While the present invention has been described in terms of preferred embodiments, it will be understood, of course, that the invention is not limited thereto since modifications may be made to those skilled in the art, particularly in light of the foregoing teachings.

The invention claimed is:

1. An endoscopic imaging device, the device comprising:
   an insertion tube comprising a proximal end and a distal end having a distal tip;
   an annular illumination tube comprising an annular illumination fiber for illuminating a vessel during endoscopy, the annular illumination tube being disposed through the insertion tube to the distal end thereof;
   a first imaging tube comprising a first imaging fiber, the first imaging fiber disposed within the annular illumination tube; a second imaging tube comprising a second imaging fiber, the second illumination fiber being disposed adjacent the first imaging tube along substantially a length of the annular illumination tube; and
   a control system in communication with the insertion tube for receiving data of a vessel and for imaging the data during operation of the device,
   wherein the control system is operable to receive video data of gross video images and image data of cellular images of the vessel from the insertion tube; convert the video data to 3-dimensional imaging data in cylindrical coordinates, and to define cylinder image data; and convert the cylinder image data to a 2-dimensional map for imaging tissues on both a gross level and a cellular level; and, an optical field of view of the first imaging tube is larger than an optical field of view of the second imaging tube.

2. The device of claim 1 further comprising a rotatable handle connected to the insertion tube, the rotatable handle being configured to rotate the insertion tube during operation of the device.

3. The device of claim 1 wherein the annular illumination fiber comprises a proximal end having an illumination adaptor connected thereto, the first imaging fiber comprising a proximal end having a first adaptor connected thereto, the second imaging fiber comprising a proximal end having a second adaptor connected thereto.

4. The device of claim 3 further comprising:
   an illumination source for illumination of the vessel, the illumination source being in communication with the annular illumination fiber by way of the illumination adaptor;
   a video imaging source for gross video imaging of the vessel, the video imaging source being in communication with the first imaging fiber by way of the first adaptor; and
   a cellular imaging source for cellular imaging of the vessel, the cellular imaging source being in communication with the second imaging fiber by way of the second adaptor.

5. The device of claim 1 wherein the second imaging tube that terminates at the distal portion of the annular illumination tube proximal to the distal tip thereof further comprises a right angle prism, and the annular illumination tube further comprises an imaging window in alignment with the right angle prism for lateral imaging in the vessel.

6. The device of claim 5 the second imaging tube further comprises a microlens disposed in alignment with and disposed between a distal end of the second imaging fiber and the right angle prism.

7. The device of claim 6 wherein the distal tip of the insertion tube is beveled.

8. The device of claim 5 wherein insertion tube further comprises a distal portion adjacent the distal end, the distal portion of the insertion tube having an imaging hole formed therethrough in longitudinal alignment with an imaging window of the annular illumination tube.

9. The device of claim 1 wherein the annular illumination fiber comprises an inner surface and an outer surface, the annular illumination tube comprising an inner tube disposed on the inner surface of the annular illumination fiber and an outer tube disposed on the outer surface of the annular illumination fiber.

10. The device of claim 1 wherein the annular illumination tube, the first imaging tube, and the second imaging tube comprises polyethylene, polypropylene, or polytetrafluoroethylene, or a mixture thereof.

11. The device of claim 1 wherein the distal end of the insertion tube is open to allow illumination from the annular illumination fiber to pass therethrough and to allow gross examination and navigation by way of the first imaging fiber during endoscopy.

12. The device of claim 1 wherein the annular illumination tube has a diameter of between about 1 and about 5 millimeters.

13. The device of claim 1 wherein a rotation angle of the insertion tube is up to 180°.

14. The device of claim 1 wherein the length of the annular illumination tube is between about 10 and 100 centimeters.

15. The device of claim 1, wherein the conversion of the video data to the 3-dimensional imaging data includes correlating a distance represented by the data of the cellular and gross images.

16. The device of claim 15 wherein the conversion of the data includes registering the video data and cylinder image data within the context of a pseudo-3-dimensional space.

17. An endoscopic imaging assembly, the assembly comprising:
   an insertion tube comprising a proximal end and a distal end having a distal tip;
   an annular illumination tube comprising an annular illumination fiber for illuminating a vessel during endoscopy, the annular illumination tube being disposed through the insertion tube to the distal end thereof, the annular illumination fiber comprising a proximal end having an illumination adaptor connected thereto;

a first imaging fiber comprising a proximal end having a first adaptor connected thereto;

a second imaging fiber comprising a proximal end having a second adaptor connected thereto;

a first imaging tube comprising a first imaging fiber for gross examination and navigation through the vessel, the first imaging fiber disposed within the annular illumination tube;

a second imaging tube comprising a second imaging fiber for cellular imaging, the second imaging tube being disposed adjacent the first imaging tube along substantially a length of the annular illumination tube;

an illumination source for illumination of the vessel, the illumination source being in communication with the annular illumination fiber by way of the illumination adaptor;

a video imaging source for gross video imaging of the vessel, the video imaging source being in communication with the first imaging fiber by way of the first adaptor;

a cellular imaging source for cellular imaging of the vessel, the cellular imaging source being in communication with the second imaging fiber by way of the second adaptor; and a control system in communication with the insertion tube for receiving data of the vessel and for imaging the data during operation of the device, wherein the control system is operable to receive video data of gross video images and image data of cellular images of the vessel from the insertion tube; convert the video data to 3-dimensional imaging data in cylindrical coordinates, and to define cylinder image data; and convert the cylinder image data to a 2-dimensional map for imaging tissues on both a gross level and a cellular level; and, an optical field of view of the first imaging tube is larger than an optical field of view of the second imaging tube.

18. The assembly of claim 17 wherein the second imaging tube terminates at the distal portion of the annular illumination tube proximal to the distal tip thereof, the second imaging tube further comprising a right angle prism disposed at the distal portion of the second imaging fiber in alignment with and distal to the second imaging fiber, the annular illumination tube further comprising an imaging window formed at the distal portion in longitudinal alignment with the right angle prism for lateral cellular imaging in the vessel.

* * * * *